United States Patent [19]
Kleiner et al.

[11] Patent Number: 6,114,340
[45] Date of Patent: Sep. 5, 2000

[54] FUNGICIDAL COMPOSITIONS

[75] Inventors: Hans-Jerg Kleiner, Kronberg; Martin Mach, Berlin; Heinz Hagemeister, Düsseldorf; Dieter Regnat, Eppstein; Herbert Buschhaus, Berlin; Hans-Peter Jende, Edewecht, all of Germany; David Stock, Cambridge; Geoffrey Gower Briggs, Harpenden, both of United Kingdom

[73] Assignee: AgrEvo UK Limited, United Kingdom

[21] Appl. No.: 09/202,967

[22] PCT Filed: Jun. 26, 1997

[86] PCT No.: PCT/GB97/01738

§ 371 Date: Feb. 3, 1999

§ 102(e) Date: Feb. 3, 1999

[87] PCT Pub. No.: WO98/00021

PCT Pub. Date: Jan. 8, 1998

[30] Foreign Application Priority Data

Jun. 28, 1996 [GB] United Kingdom ................ 9613637

[51] Int. Cl.[7] .......................... A01N 43/54; A01N 57/00; A01N 57/18
[52] U.S. Cl. .......................... 514/259; 514/107; 514/108; 514/114; 514/129; 514/140; 514/141; 514/269
[58] Field of Search ................ 514/259, 269, 514/107, 108, 114, 129, 140, 141

[56] References Cited

U.S. PATENT DOCUMENTS 2,570,503 10/1951 Tawney ................................ 260/461

FOREIGN PATENT DOCUMENTS

| 955050 | 12/1956 | Germany . |
| 245322 | 3/1975 | Germany . |
| 4339120A1 | 5/1995 | Germany . |
| 93/04585 | 3/1993 | WIPO . |
| 95/13702 | 5/1995 | WIPO . |

OTHER PUBLICATIONS

Chemical Abstracts, vol. 75, No. 7, 1971 Columbus, Ohio, US; Abstract No. 49254, A.N. Pudovik, et al.: "Reaction of phosphonites and phosphinites with tin tetrachlorides".

Chemical Abstracts, vol. 92, No. 20, 1980 Columbus, Ohio, US; Abstract No. 166963, R.R. Shoun, et al.: "Bidentate organophosphorus compounds as extractants from acidic waste solutions".

Y. Xu, et al.: "Studies on N,N–disubstituted dialkyl 2–aminophosposhonates and derivatives thereof"; Synthesis, vol. 5, 1990, Stuttgart, Germany, pp. 427–429.

Chemical Abstracts, vol. 62, No. 1, 1965 Columbus, Ohio, US; Y. Y. Hsu, et al.: "Organophosphorus compounds. III. Dialkyl N,N–disubstituted aminomethylphosphonates and their derivatives"; col. 1317c.

*Primary Examiner*—Allen J. Robinson
*Attorney, Agent, or Firm*—Ostrolenk, Faber, Gerb & Soffen, LLP

[57] ABSTRACT

An improved fungicidal composition is a mixture of (a) fungicide used to combat phytopathogenic fungi and (b) at least one phosphonate or phosphinate of formula $R^1R^2P(O)OR^3$ where $R^1$ is $C_{6-20}$alkyl, $C_{6-20}$alkoxy or optionally substituted phenyl, $R^2$ is benzyl, $C_{6-20}$alkyl optionally interrupted by NH or O, di-$C_{6-20}$alkylamino or the group —$CH_2CH_2$—$R^1P(O)OR^3$, and $R^3$ $C_{6-20}$alkyl. Some of the compounds of formula (I) are novel.

19 Claims, No Drawings

FUNGICIDAL COMPOSITIONS

This application is a 371 of PCT/GB97/01738, filed Jun. 26, 1997.

FIELD OF THE INVENTION

This invention relates to new fungicidal compositions.

PRIOR ART

U.S. Pat. No. 2,927,014 discloses phosphonates and phosphinates having herbicidal activity. In WO 9418837 and WO 9304585, it is disclosed that certain phosphonates can enhance the activity of specified herbicides. We have now found that such compounds can also be used with advantage in association with certain fungicides used to combat phytopathogenic fungi.

DESCRIPTION

The invention provides a fungicidal composition which comprises a mixture of (a) fluquinconazole or azoxystrobin, and (b) at least one phosphonate or phosphinate of formula I

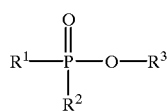

(I)

where $R^1$ is $C_{6-20}$-alkyl, $C_{6-20}$-alkoxy or optionally substituted phenyl $R^2$ is benzyl, $C_{6-20}$-alkyl, optionally interrupted by NH or O, di-$C_{6-20}$-alkylamino or the group

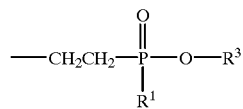

and $R^3$ is $C_{6-20}$-alkyl.

Phosphonates of formula I wherein $R^1$ is $C_6$–$C_{20}$-alkoxy and $R^2$ is $C_6$–$C_{20}$-alkyl are known. They are made for example according the disclosure in DE 1,963,014.

Phosphinates of formula I wherein $R^1$ is $C_6$–$C_{20}$-alkyl and $R^2$ is phenyl can be prepared by catalytically induced addition of olefins to phenyl monoalkylphosphonites which are preferably prepared as described in DE patent 196 041 95.

Ethane-1,2-diphosphonic acid tetraalkyl esters of formula I wherein $R^1$ is $C_6$–$C_{20}$-alkoxy and $R^2$ is the group

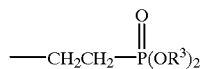

can be made by addition of the appropriate phosphonates to a dialkyl vinylphosphonate in the presence of basic catalysts such as sodium methylate or sodium hydride.

Alkyl- or dialkylaminoalkylphosphonic acid dialkyl esters of the formula

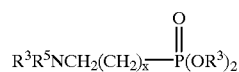

wherein $R^3$ is as defined above and $R^5$ is $R^3$ or hydrogen and x is 0 or 1 can be prepared according to two different methods. Compounds wherein x is 0 are made according to the following equation

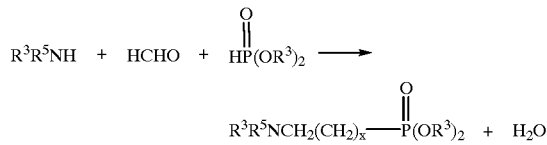

Compounds wherein x is 1 and made according to the following equation:

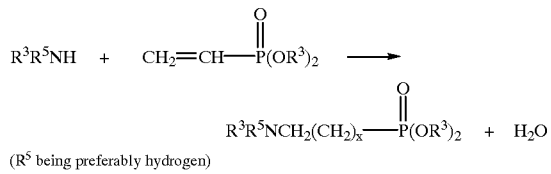

($R^5$ being preferably hydrogen)

The addition of the amine is made in the presence of basic catalysts such as sodium methylate of sodium hydride according to the process described by A. N. Pudovik et al., Doklady Akad. S.S.S.R. 80365(1951); (A 50, 4143(1956).

Azoxystrobin is the common name for the fungicide methyl (E)-2-{2-[6-(2-cyanophenoxy)pyrimidin-4-yloxy]phenyl}-3-methoxyacrylate and fluquinconazole is the common name for the fungicide 3-(2,4-dichlorophenyl)-2-(1H-1,2,4-triazol-1-yl)-4(3H)-quinazolinone).

We have found that phosphonates of formula I, which have little or no activity in their own right considerably enhance the fungicidal activity of fluquinconazole and azoxystrobin.

The weight ratio of component a) to b) is generally between 10:1 and 1:10, preferably between 3:1 and 1:5.

The compound of formula I can be added to conventional formulations of component a). It may be desirable to also add small quantities of solvent and/or surfactant especially a non-ionic surfactant, and other additives such as fatty acids to improve the emulsifiability of the compound of formula I.

The following Examples illustrate the invention. Examples 1 to 6 describe the preparation of what are believed to be novel phosphonates and phosphinates, which can be used in admixture with azoxystrobin or fluquinconazole.

EXAMPLE 1

Into a reaction vessel, which was heated to 100° C., with a reflux condenser (−15° C.), were simultaneously added aqueous formaldehyde (12.17 g of 37% solution) and a mixture of di(2-ethylhexyl)amine (36.22 g) and di(2-ethylhexyl) phosphonate (45.96 g). The mixture was heated for 1 hour with stirring and then cooled to 20° C. The water was removed by distillation under reduced pressure to give di(2-ethylhexyl){[di(2-ethylhexyl)amino]methyl}phosphonate, as a colourless liquid ($n_D^{20}$=1.4563).

EXAMPLE 2

A mixture of 2-ethylhexyl vinylphosphonate, 2-ethylhexylamine (66.50 g) and sodium hydride (0.10 g)

was stirred at 130° C. for 6 hours. After addition of an additional amount of sodium hydride (0.10 g) and stirring 9 hours there was obtained di(2-ethylhexyl){[2-ethylhexyl)amino]methyl}phosphonate, as a colourless liquid ($n_D^{20}$=1.4537).

EXAMPLE 3

To a mixture of 2-ethylhexyl vinylphosphonate (49.9 g), di(2-ethylhexyl) phosphonate (45.9 g) and THF (80 ml) was added to 20° C. with stirring, a solution of sodium methylate in methanol until the mixture reached pH 8–9. The mixture was stirred for 12 hours and water (100 ml) and ethyl acetate (200 ml) added. The organic phase was separated, dried with sodium sulfate, filtered and the solvent evaporated under reduced pressure to give tetra(2-ethylhexyl) ethane-1,2-diphosphonate as a colourless liquid, $n_D^{20}$=1.4488.

EXAMPLE 4

A mixture of 2-ethylhexyl vinylphosphonate (49.90 g), octadecylamine (40.43 g) and sodium hydride 0.10 g was stirred at 140° C. for 6 hours. Water (100 ml) and ethyl acetate (200 ml) were added. The organic phase was separated, dried with sodium sulfate, filtered and the solvent evaporated under reduced pressure to give di(2-ethylhexyl) [2-(octadecylamino)ethyl]phosphonate, as colourless liquid $n_D^{40}$=1.4541.

EXAMPLE 5

A mixture of tetradec-1-ene (30.05 g) and benzoyl peroxide (0.3 g) was added dropwise with stirring to 2-ethylhexyl phenylphosphonate (38.95 g) at 160° C. The resulting mixture was stirred for 6 hours to give 2-ethylhexyl phenyl tetradecylphosphinate, as a colourless liquid $n_D^{20}$=1.4813.

EXAMPLE 6

In a similar manner to example 5, starting from octadec-1-ene, there was obtained 2-ethylhexyl phenyl octadecylphosphinate, as colourless liquid $n_D^{20}$=1.4729.

EXAMPLE 7

Wheat plants were inoculated with *Erysiphe graminis* (powdery mildew). One day after inoculation, they were sprayed with fluquinconazole, obtained by diluting with water to the desired concentration, a suspension concentrate comprising 50% by weight active ingredient, at a rate of 50 g fluquinconazole/ha either alone or mixed with various inactive phosphonate or phosphinate esters added at a concentration of 0.1% v/v, together with an appropriate emulsifier.

One week after spraying, the wheat was assessed for control of disease. The results are as follows:

| Phosphonate/phosphinate added | % control |
|---|---|
| dihexyl octylphosphonate | 97.2 |
| dioctyl octylphosphonate | 100 |
| di(2-ethylhexyl) hexylphosphonate | 100 |
| di(2-ethylhexyl) octylphosphonate | 100 |
| di(2-ethylhexyl) decylphosphonate | 100 |
| di(2-ethylhexyl) dodecylphosphonate | 100 |
| di(2-ethylhexyl) tetradecylphosphonate | 100 |
| 2-ethylhexyl phenyl tetradecylphosphinate (Example 5) | 100 |
| tetra(2-ethylhexyl) ethane-1,2-diphosphonate (Example 3) | 100 |
| 2-ethylhexyl phenyl octadecylphosphinate (Example 6) | 100 |
| di(2-ethylhexyl) {[di(2-ethylhexyl)amino]methyl}phosphonate (Example 1) | 85.2 |
| di(2-ethylhexyl) [2-(octadecylamino)ethyl]-phosphonate (Example 4) | 93.5 |
| nil | 0 |

EXAMPLE 8

In a similar manner, Example 7 was repeated with some of the phosphonates and with replacing fluquinconazole with azoxystrobin. The results are as follows

| active ingredient | Rate (g/ha) | Phosphonate | Rate (% v/v) | control (%) |
|---|---|---|---|---|
| azoxystrobin | 62.5 | — | — | 29 |
| azoxystrobin | 125 | — | — | 30 |
| azoxystrobin | 250 | — | — | 94 |
| azoxystrobin | 62.5 | di(2-ethylhexyl) octylphosphonate | 0.2 | 98 |
| azoxystrobin | 125 | di(2-ethylhexyl) octylphosphonate | 0.2 | 100 |
| azoxystrobin | 250 | di(2-ethylhexyl) octylphosphonate | 0.2 | 100 |
| azoxystrobin | 62.5 | compound of Example 4 | 0.2 | 100 |
| azoxystrobin | 125 | compound of Example 4 | 0.2 | 100 |
| azoxystrobin | 250 | compound of Example 4 | 0.2 | 100 |

EXAMPLE 9

Example 7 was repeated in test against *Puccinia recondita* using azoxystrobin

Results are as follows:

| active ingredient | Rate (g/ha) | Phosphonate | Rate (% v/v) | control (%) |
|---|---|---|---|---|
| azoxystrobin | 1 | — | — | 8 |
| azoxystrobin | 5 | — | — | 9 |
| azoxystrobin | 20 | — | — | 23 |
| azoxystrobin | 1 | di(2-ethylhexyl) octylphosphonate | 0.2 | 29 |
| azoxystrobin | 5 | di(2-ethylhexyl) octylphosphonate | 0.2 | 85 |
| azoxystrobin | 20 | di(2-ethylhexyl) octylphosphonate | 0.2 | 91 |
| azoxystrobin | 1 | compound of Example 4 | 0.2 | 79 |
| azoxystrobin | 5 | compound of Example 4 | 0.2 | 90 |
| azoxystrobin | 20 | compound of Example 4 | 0.2 | 93 |

EXAMPLE 10

The following are typical formulations incorporating fluquinconazole and the preferred phosphonate according to the invention.

a) an SC formulation was made from the following components

| Ingredient | g/l |
|---|---|
| fluquinconazole | 100 |
| di(2-ethylhexyl) octylphosphonate | 320 |
| emulsifiers | 190 |
| buffer | 10 |
| structuring agent | 30 |
| vegetable oil to volume | 327 | b) a suspoemulsion was made to the following composition.

| Ingredient | g/l |
| --- | --- |
| fluquinconazole | 54 |
| prochloraz | 174 |
| dispersant | 25 |
| emulsifiers | 180 |
| buffer | 10 |
| crystal growth inhibitor | 38 |
| di(2-ethylhexyl) octylphosphonate | 174 |
| aromatic hydrocarbon solvent | 192 |
| propylene glycol | 40 |
| antifoam | 2 |
| biocide | 2 |
| structuring agent | 7.5 |
| water to volume | 176 |

What is claimed is:

1. A fungicidal composition which comprises a mixture of
(a) a fungicidally effective amount of fluquinconazole or azoxystrobin and
(b) an enhancing effective amount of at least one phosphonate or phosphinate of formula I

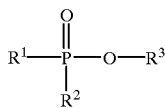

(I)

where
$R^1$ is $C_{6-20}$-alkyl, $C_{6-20}$-alkoxy or optionally substituted phenyl
$R^2$ is benzyl, $C_{6-20}$-alkyl, optionally interrupted by NH or O, di-$C_{6-20}$-alkylamino or the group

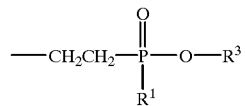

and
$R^3$ is $C_{6-20}$-alkyl.

2. A fungicidal composition according to claim 1, wherein $R^1$ is $C_{6-20}$alkyl, and $R^2$ is $C_{6-20}$alkyl optionally interrupted by NH.

3. A fungicidal composition according to claim 2, containing one or two 2-ethylhexyl groups.

4. A fungicidal composition according to claim 3, wherein (b) is di(2-ethylhexyl)octyl phosphonate.

5. A fungicidal composition according to claim 4, wherein (a) is azoxystrobin.

6. A fungicidal composition according to claim 5, wherein the ratio of (a) to (b) is between 1:10 and 10:1 by weight.

7. A fungicidal composition according to claim 6, wherein the ratio of (a) to (b) is between 3:1 and 1:5.

8. A fungicidal composition according to claim 3, wherein (b) is di(2-ethylhexyl)[2-(octadecylamino)ethyl] phosphonate.

9. A fungicidal composition according to claim 3, wherein (a) is fluquinconazole.

10. A fungicidal composition according to claim 1, wherein (a) is fluquinconazole.

11. A fungicidal composition according to claim 1, wherein (a) is azoxystrobin.

12. A fungicidal composition according to claim 1, wherein the ratio of (a) to (b) is between 1:10 and 10:1 by weight.

13. A fungicidal composition according to claim 1, wherein the ratio of (a) to (b) is between 3:1 and 1:5 by weight.

14. A method of augmenting the activity of the fungicides fluquinconazole or azoxystrobin used to combat phytopathogenic fungi which comprises employing a fungicidally effective amount of said fungicides in combination with an enhancing effective amount of at least one phosphonate or phosphinate of the formula $R^1R^2P(O)OR^3$ where $R^1$ is $C_{6-20}$alkyl, $C_{6-20}$alkoxy or optionally substituted phenyl, $R^2$ is benzyl, $C_{6-20}$alkyl, optionally interrupted by NH or O, di-$C_{6-20}$alkylamino or the group —$CH_2CH_2$—$R^1P(O)OR^3$, and $R^3$ is $C_{6-20}$alkyl.

15. The method of claim 14, wherein $R^1$ is $C_{6-20}$alkyl, and $R^2$ is $C_{6-20}$alkyl optionally interrupted by NH.

16. The method of claim 15, wherein the phosphonate or phosphinate contains one or two 2-ethylhexyl groups.

17. The method of claim 16, wherein the fungicide is azoxystrobin and is agumented by di(2-ethylhexyl)octyl phosphonate.

18. The method of claim 14, wherein the ratio of the fungicide to said at least one phosphonate or phosphinate is between 1:1 and 1:10 by weight.

19. The method of claim 14, wherein the ratio of the fungicide to said at least one phosphonate or phosphinate is between 3:1 and 1:5 by weight.

* * * * *